United States Patent [19]

Phadnis et al.

[11] Patent Number: 5,316,946
[45] Date of Patent: May 31, 1994

[54] DNA TRANSPOSON TN5SUPF IN PLASMID PBRG1310

[75] Inventors: Suhas H. Phadnis, St. Louis; Henry V. Huang, University City; Doulgas E. Berg, St. Louis, all of Mo.

[73] Assignee: Washington University, St. Louis, Mo.

[21] Appl. No.: 468,450

[22] Filed: Jan. 22, 1990

Related U.S. Application Data

[63] Continuation-in-part of Ser. No. 105,422, Oct. 5, 1987, Pat. No. 5,137,829.

[51] Int. Cl.$^5$ .................... C12N 15/63; C12N 15/70
[52] U.S. Cl. .................... 435/320.1; 435/172.3; 435/252.33; 536/24.2
[58] Field of Search ............... 435/320.1, 235.1, 252.3, 435/172.3; 935/29, 79

[56] References Cited

U.S. PATENT DOCUMENTS 4,716,105  12/1987  Mizuuchi et al. ............... 435/320.1

OTHER PUBLICATIONS

Seed et al. (1983), Nucleic Acid Research, vol. 11, pp. 2427–2445.
Vermersch et al. (1987), Gene, vol. 54, pp. 229–238.
Ubben et al. (1986), Gene, vol. 41, pp. 145–152.
Phadnis et al. (1987), Proc. Natl. Acad. Sci., vol. 84, pp. 9118–9122.
Levinson et al. (1984), J. Mol. App. Genet.; vol. 2, Abstract only.
Berg et al., Genetics 105, 813–828 (1983).
Berg and Berg, Bio/Technology 1, 417–435 (1983).
Berg and Berg, in Neidhardt et al., *E. coli and S. typhimurium:* Cellular and Mol. Biol., 1071–1109 (1987).
Johnson and Resnikoff, Nature 304, 280–282 (1983).
Sasakawa et al., Proc. Natl. Acad. Sci. U.S.A. 80, 7293–7297 (1983).
Auserwald et al., Cold Spring Harbor Symp. Quant. Biol. 45, 107–113 (1983).
Krebs and Reznikoff, J. Mol. Biol. 192, 781–791 (1986).
Melton et al., Nucl. Acids. Res. 12, 7035–7056 (1984).
Studier and Moffatt, J. Mol. Biol. 189, 113–130 (1986).
Egelhoff et al., DNA 4, 241–248 (1985).
Phadnis, Huang & Berg, Proc. Natl. Acad. Sci. U.S.A. 86, 5908–5912 (1989).
Berg, in Mobile DNA, eds. Berg & Howe (ASM), Ch. 6, pp. 185–210 (1989).

*Primary Examiner*—Richard A. Schwartz
*Attorney, Agent, or Firm*—Scott J. Meyer

[57] ABSTRACT

A small, novel transposon useful for mutagenesis and sequencing DNAs cloned in phage λ is disclosed which comprises a transposon having at each terminus a segment of 19 nucleotides selected from the group consisting of the O-end and I-end sequences of Tn5, at least one restriction enzyme site positioned less that 20 nucleotides distant from each said terminal segment, and a supF amber-suppressor tRNA gene insert.

1 Claim, 4 Drawing Sheets

Tn5 supF

FIG. 1A

```
                                        BamHI
1   CTGACTCTTATACACAAGTAGGGGATCCTAATTCTTTCTAACGT    45
    GACTGAGAATATGTGTTCATCCCCTAGGATTAAGAAAGAGTTGCA
                  O primer 46  AACACTTTACAGCGGCGCGTCATTTGATATGATGCGCCCCGCTTC    90
    TTGTGAAATGTCGCCGCGCAGTAAACTATACTACGCGGGGCGAAG

|supF tRNA 5' end
91  CCGATAAGGGAGCAGGCCAGTAAAAGCATTACCCGTGGTGGGGTT   135
    GGCTATTCCCTCGTCCGGTCATTTTCGTAATGGGCACCACCCCAA 136 CCCGAGCGGCCAAAAGGGAGCAGACTCTAAATCTGCCGTCATCGAC   180
    GGGCTCGCCGGTTTCCCTCGTCTGAGATTTAGACGGCAGTAGCTG supF tRNA 3'end|
181 TTCGAAGGTTCGAATCCTTCCCCCACCACCATCACTTTCAAAAGT    225
    AAGCTTCCAAGCTTAGGAAGGGGGTGGTGGTAGTGAAAGTTTTCA I primer
226 CCGAAAGAATTAGGATCCCGAGATCTGATCAAGAGACAG          264
    GGCTTTCTTAATCCTAGGGCTCTAGACTAGTTCTCTGTC
                     BamHI
```

DNA TRANSPOSON TN5SUPF IN PLASMID PBRG1310

"This invention was made with Government support under Grant No. 37138 awarded by the National Institutes of Health. The Government has certain rights in the invention."

CROSS-REFERENCE TO RELATED APPLICATION

This is a continuation-in-part of application Ser. No. 07/105,422, filed Oct. 5, 1987, now U.S. Pat. No. 5,137,829.

BACKGROUND OF THE INVENTION

This invention relates to a DNA segment or vector system useful for mutagenesis and sequencing DNAs cloned in phage λ and, more particularly, to a small, novel prokaryotic transposon.

It is known that certain complex DNA segments, known as transposons, are able to insert into many sites in the genome of their host organisms. That is, certain large segments of DNA called insertion sequences (ISs) when present in closely spaced pairs can move as a unit, carrying along the genes lying between them. These complex units constitute the transposon. They exist in prokaryotes, such as bacteria, as well as in eukaryotes.

Recently, a useful bacterial transposon referred to as Tn5 was discovered and characterized. It is a discrete 5.8 kilobase (kb) segment of bacterial DNA which can insert at high frequency into numerous sites in the chromosomes, plasmids, and temperate phages of gram negative bacteria. It encodes resistance to the aminoglycoside antibiotics, kanamycin and neomycin, in bacteria, and G418 (geneticin) in eukaryotic cells. The restriction enzyme map of Tn5 is illustrated by Berg et al., *Genetics* 105, 813-828, (1983). Further background information on this Tn5 can be had by reference to the recent review articles by Berg and Berg, *Bio/Technology* 1, 417-435 (1983); Berg and Berg in Neidhardt et al., (eds.), "*Escherichia coli* and *Salmonella typhimurium*: Cellular and Molecular Biology," Amer. Soc. Microbiol., Washington, D.C., Ch. 63, pp. 1071-1109 (1987); and Berg, in *Mobile DNA*, eds. Berg & Howe (Am. Soc. Microbiol., Wash., D.C.), Ch. 6, pp. 185-210 (1989).

Much of the power of modern molecular genetics stems from efficient means of generating easily characterized mutations and from the ability to determine DNA sequences with efficiency and precision. Two widely used methods for DNA sequence analysis are the base-specific chemical cleavage method [Maxam and Gilbert, *Methods Enzymol.* 65, 499-560 (1980)] and the enzymatic chain termination method [Sanger et al., *Proc. Natl. Acad. Sci. USA* 74, 5463-5467 (1977)]. In the frequently used chain-termination method, short oligonucleotides are used to prime in vitro DNA synthesis from specific sites in template DNA in the presence of chain-terminating dideoxynucleotides. Up to 1 kilobase (kb) of DNA can be read from a single primer [Innis et al., *Proc. Natl. Acad. Sci. USA* 85, 9436-9440 (1988), but additional manipulations are needed to sequence longer stretches of DNA - e.g. random subcloning, the isolation of nested deletions, or the repeated synthesis of oligonucleotide primers [Barnes et al., *Methods Enzymol.* 65, 98-122 (1980); Henikoff, *Ibid.* 155, 156-165 (1988); Strauss et al., *Anal. Biochem.* 154, 353-360 (1986). In alternative strategies transposons have been inserted into many sites in target DNAs in plasmids, and unique DNAs close to their ends have been used as binding sites for DNA sequencing primers [See copending application Ser. No. 07/105,422, filed Oct. 5, 1987; Nag et al., *Gene* 64, 135-145 (1988); Berg et al., in *Mobile DNA*, eds. Berg & Howe (Am. Soc. Microbiol., Wash., D.C.) pp. 879-925 (1989); Adachi et al., *Nucleic Acids Res.* 15, 771-784 (1987); Ahmed, *Methods Enzymol.* 155, 177-204 (1987); and Liu et al., *Nucleic Acids Res.* 15, 9461-9469 (1987)]. Transposons have not, in contrast, been used to sequence DNAs cloned in phage λ, because most λ cloning vectors grow only lytically and kill their infected host cells, whereas the resistance markers in most transposons are generally used by selecting for cells that form colonies in the presence of antibiotic. In addition, insertion of a several-kilobase long transposon into very large recombinant phage DNAs would make the phage inviable.

BRIEF DESCRIPTION OF THE INVENTION

In accordance with the present invention a small, novel prokaryotic transposon for mutagenesis and sequencing of DNAs cloned in phage λ is provided. This novel vector system is a derivative of transposon Tn5. It consists of a transposable DNA unit comprising at each terminus a segment of 19 nucleotides selected from the group consisting of the O-end and I-end sequences of the Tn5 transposon, at least one restriction enzyme site positioned less than about 20 nucleotides distant from each said terminal segment, and a supF amber-suppressor tRNA gene insert.

In a preferred embodiment of the invention, referred to herein as Tn5supF, the transposon is only 264 base pairs (bp) long in contrast to the nearly 6 kb of wild-type Tn5, and has an O-end segment at one terminus and an I-end segment at the other terminus of the double stranded transposon DNA. Transposition of Tn5supF to λ is easily selected, inserts are widely distributed in target DNAs, and Tn5supF inserts facilitate the sequencing of DNAs in λ phage. Its insertion into λ can be selected by plaque formation by using nonsuppressing (sup⁰) *Escherichia coli* for amber mutant λ phage and sup⁰ dnaB-amber P1 ban *E. coli* for nonamber λ phage. It transposes efficiently and inserts quasi-randomly into DNA targets. The unique sequences near its termini can be used as primer binding sites for dideoxynucleotide DNA sequencing, thus permitting the direct sequencing of DNAs cloned in phage λ without subcloning.

It should be understood that the DNA used in the novel transposon of this invention is double-stranded. Due to the complementary nature of DNA base-pairing, the nucleotide sequence of one strand of a double-stranded DNA molecule is sufficient to determine the sequence of the opposing strand.

The 19 base pair long terminal sequences of the novel transposon, the O-end and I-end, are well-known and defined as follows:

O-end sequence
5' CTGACTCTTATACACAAGT
3' GACTGAGAATATGTGTTCA

See, e.g., Berg and Berg, *Bio/Technology* 1, 417-435 (1983); Johnson and Reznikoff, *Nature* 304, 280-282 (1983); and Saskawa et al., *Proc. Natl. Acad. Sci. USA* 80, 7293-7297 (1983).

I-end sequence
5' CTGTCTCTTGATCAGATCT
3' GACAGAGAACTAGTCTAGA see Sasakawa et al., Ibid.

Restriction enzyme sites should be located near each of said termini. They can be directly adjacent to (flush) or within about 20 nucleotides distant from the terminal segments. They can be the same or different at each end and are illustrated, for example, by the BamHI sites 5' GGATCC. Additional restriction enzyme sites can be inserted in the transposon as may be desired for particular applications. Any of the common restriction endonucleases can be employed for these purposes.

The supF amber-suppressor tRNA gene used in this invention is a well known selectable marker described by Seed, *Nucleic Acids Res.* 11, 2427–2445 (1983).

A preferred DNA cloning vector containing the Tn5supF transposon of the present invention is plasmid pBR1310. This plasmid carried in strain DB4496, a derivative of *E. coli* K-12 which also harbors plasmid p3, was deposit at the American Type Culture Collection, Rockville, Md., under accession number ATCC 68201, on Jan. 5, 1990.

A useful starting material for the present invention is plasmid pBRG1306, which is a known pBR322-derived multicopy plasmid that contains the 19-bp O- and I-end segments of IS50 as described by Phadnis and Berg, *Proc. Natl. Acad. Sci. USA* 84, 9118–9122 (1987). Plasmid pBR322 is a well characterized, commercially available cloning vector having a molecular weight of $2.6 \times 10^6$. It is the workhorse of molecular biology, recently reviewed by Balbas et al., Gene 50, 3–40 (1987), and its sequence and restriction enzyme map has been published by Maniatis et al., *Molecular Cloning: A Laboratory Manual*, Cold Spring Harbor Laboratory, Cold Spring Harbor, N.Y. (1982). An amended sequence is described by Peden, *Gene* 22, 277–280 (1983).

The *E. coli* supF gene can be inserted into pBRG1306 to generate plasmid pBRG1308. The Tn5supF is then shifted back to a low copy number plasmid derived from the F factor of *E. coli* to generate plasmid pBRG1310.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention in conjunction with the appended drawings, in which briefly:

BRIEF DESCRIPTION OF THE DRAWINGS

FIG. 2 shows the restriction map of the pBRG1310 plasmid containing Tn5supF. Thick line in plasmid, an 8.7-kb EcoRI-HindIII fragment (HindIII site is filled-in) from pDF41; thin line including Tn5supF on expanded scale, a 3.4-kb EcoRI-Tth111I (Tth111I is filled-in) fragment from pBRG1308; solid and open boxes in the expanded scale diagram of Tn5supF are as in FIG. 1A. The estimated position of restriction sites (clockwise from the EcoRI site, in bp) are: SalI 135; KpnI, 2591; KpnI, 5940; BamHI, 6708; ClaI, 7082; ClaI, 8242; SalI, 8878; SalI, 10,413; KpnI, 11,513; SacI, 11,803; EcoRI, 12,133. The restriction fragment lengths were deduced from well-known, nucleotide sequences of pDF41 [GenBank® nucleotide sequence bank Accession M12987; restriction map published by Kahn et al., *Methods Enzymol.* 68, 268–280 (1979)], pBRG1306 [Phadnis & Berg, *Proc. Natl. Acad. Sci. USA* 84, 9118–9122 (1987 and the supF gene [Seed, *Nucleic Acids Res.* 11, 2427–2445 (1983)], and verified by restriction digests. In these coordinates Tn5supF extends between positions 11,518 and 11,783. The F origin of replication is between two KpnI sites (positions 2591 and 5940).

FIG. 3 shows the restriction mapping of Tn5supF insertion. The DNAs of six Charon 4A::Tn5supF phage obtained after a single cycle of growth on strain DB4495 and plating for single plaques on the sup° strain MC1061 were digested with EcoRI and BamHI and electrophoresed in an agarose gel. Lanes: WT, parental Charon 4A; 1–6, Charon 4A::Tn5supF phage. The DNAs in lanes 3 and 5 may be from a single transposition event. The absence of the 6.6-kb EcoRI-BamHI fragment of Charon 4A from each of the six Tn5supF-containing phage indicates that in each case the insert is in the same 6.6-kb region. This type of restriction analysis can be used to choose particular insertions for subsequent sequencing.

FIG. 4 is a diagrammatic representation which shows the positions of independent Tn5supF insertions in Charon 4A. The 14.3-kb stuffer region of Charon 4A, between the essential λ genes J and N, contains most of the sequences in this phage that are not needed for plaque formation and was taken as representative of cloned DNA sequences. The Tn5supF insertions were obtained after single cycles of infection of strain DB4595 and selection of suppressor-containing phage on sup° strain MC1061. The phage with inserts designated as subset I (inserts 1−6) made LacZ− plaques on 5-bromo-4-chloro-3-indolyl β-D-galactoside (X-gal) indicator agar, whereas phage designated as subset II made Lac+ plaques on X-gal agar. All 16 insertions tested were in the 14.3-kb stuffer region; insertions 1–12 were sequenced (see Table 2), and the positions of the remaining four were estimated by digestion with EcoRI, BamHI, and HindIII.

Standard biochemical nomenclature is used herein in which the nucleotide bases are designated as adenine (A); thymine (T); guanine (G); and cytosine (C). N connotes any of these nucleotides while Py refers to pyrimidine nucleotides and Pu refers to purine nucleotides. Corresponding nucleotides are, for example, deoxyadenosine-5'-triphosphate (dATP). As is conventional for convenience in the structural representation of a DNA nucleotide sequence, only one strand is usually shown in which A on one strand connotes T on its complement and G connotes C.

Commonly available restriction endonucleases used herein have the following restriction sequences and (indicated by arrows) cleavage patterns.

In order to illustrate specific preferred embodiments of the invention in further detail, the following exemplary laboratory preparative work was carried out.

EXAMPLE

Materials and Methods

Figure 1A:
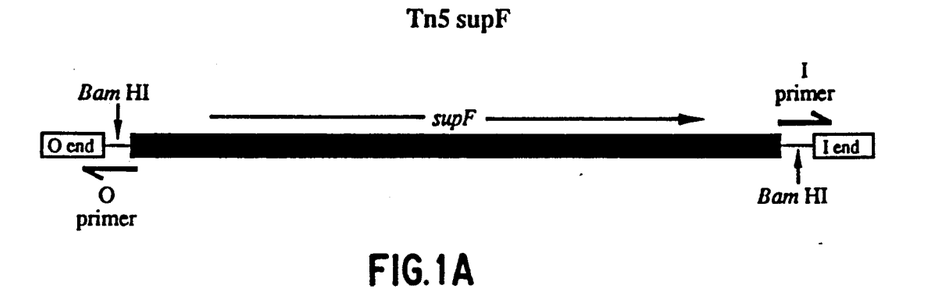
FIG. 1A is a diagrammatic representation which shows the structure of the transposon Tn5supF in a preferred embodiment of the invention.
Figure 1B:
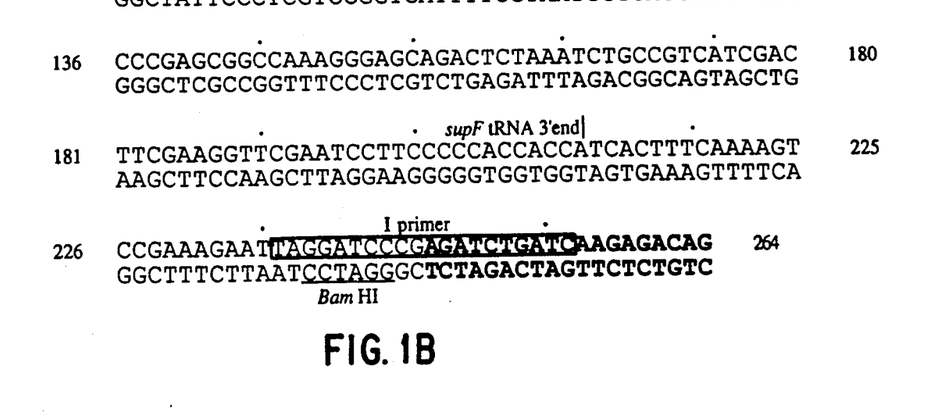
FIG. 1B shows the complete 264 bp nucleotide sequence of Tn5supF. The 19 bp at each end correspond to the O- and I-end segments of IS50 that are needed for transposition. Boxed sequences indicate the primers used for sequencing outward from the O and I ends. The 5' and 3' ends of the mature (processed) supF tRNA product are indicated, but sequences needed for tRNA synthesis and processing extend from position 52 to position 231.

Strains and General Techniques. The bacterial strains, plasmids, and λ phage derivatives used herein are listed in Table 1. The media and conditions for bacterial and phage growth, DNA extractions, and recombinant DNA cloning were conventional as described previously by Phadnis et al., *Proc. Natl. Acad. Sci. USA* 84, 9118–9122 (1987); Maniatis et al., *Molecule Cloning: A Laboratory Manual*, Cold Spring Harbor Lab., Cold Spring Harbor, N.Y. (1982); and Egner et al., *Proc. Natl. Acad. Sci. USA* 78, 459–463 (1981). The following oligonucleotides were used: O primer, 5'-TAGGATCCCCTACTTGTGTA for sequencing from the "outside" (O) end of Tn5supF into adjacent target DNA; I primer, 5'-TAGGATCCCGAGATCT-GATC, for sequencing from the inside (I) end of Tn5supF into adjacent target DNA (see FIG. 1); and 5'-CTGGCACGCGCTGGACGCG, specific for vector sequences 30 bp upstream of the Tn5supF I end of plasmids pBRG1308 and pBRG1310, for verifying the sequence of Tn5supF. Plasmid p3 was transferred between strains by conventional conjugation as described previously by Seed, *Nucleic Acids Res.* 11, 2427–2445 (1983).

TABLE 1

| Bacterial and plasmid strains | |
|---|---|
| Name | Description/derivation |
| Bacterial strain | |
| DB973 | supF |
| DB4494 | MC1061 [p3] [pBRG1308] |
| DB4495 | MC1061 [p3] [pBRG1310] |
| DB4496 | MC1061 dam::Tn9 [p3] [pBRG1310] |
| MC1061 | F⁻ sup° |
| DK21 | sup° dnaBam266 (λimm21-banP1) cold sensitive |
| Plasmid | |
| p3 | kan$^R$ ampam tetam, conjugative |
| pDF41 | miniF (single copy) trpE |
| pBRG1306 | pBR322 derivative amp$^R$, contains O and I ends of IS50 |
| pBRG1308 | supF gene from Proteus 13 in BamHI site of pBRG1306 |
| pBRG1310 | pDF41-Tn5supF, tnp nearby |
| Proteus 13 | pBR322 derivative, supF in a 211-bp Alu 1 fragment |
| Phage | |
| Charon 4A | Aam32 Bam1 lac5 bio256 KH54 nin5 |
| λb221 cI857 | | kan$^R$, Kanamycin resistance; amp, ampicillin; tet, tetracycline.
*pDF41 was isolated as a 12.7-kb EcoRI fragment from pDF42, a chimaera that had been made by joining pDF41 to a derivative of the multicopy colE1 plasmid Construction of Tn5supF. A small Tn5-related transposon containing the supF suppressor tRNA gene as its selectable marker (FIG. 1A) was constructed starting with the pBR322-derived multicopy plasmid pBRG1306 [Phadnis et al., supra.]. This plasmid contains the 19-bp O- and I-end segments of IS50(Tn5) that are needed as sites for transposition and the transposase (tnp) gene (for review, see Berg in Mobile DNA, eds. Berg & Howe, Am. Soc. Microbiol., Washington, D.C., pp. 185–210 (1989). pBRG1306 DNA was digested with BamHI, which cleaves between the O- and I- end segments in this plasmid, the recessed 3' DNA ends were filled using the Klenow fragment of DNA polymerase I, and the resultant linear DNA was ligated with a 211-bp Alu I fragment containing a synthetic *E. coli* supF gene from plasmid Proteus 13 to generate plasmid pBRG1308. BamHI sites flanking supF are regenerated by this ligation. Plasmid pBRG1308 was selected by transformation of the nonsuppressing strain MC1061 [Casadaban & Cohen, *J. Mol. Biol.* 138, 179–207 (1980)] carrying the compatible p3 plasmid (which contains amber mutations in amp and tet genes; see Seed, supra.) to tetracycline resistance (suppression of the tet amber allele), and the sequence of Tn5supF (FIG. 1B) was verified by the chain-termination DNA sequencing method of Sanger using reverse transcriptase on denatured double-stranded DNA [Zagursky et al., *Gene Anal. Tech.* 2, 89–94 (1985)]. Preliminary tests showed that this element could transpose to phage λ.

Most cells in young cultures of strain DB4494, which carries Tn5supF on a multicopy plasmid, made small colonies. These cultures were usually overgrown by healthier cells during overnight incubation with or without tetracycline to select for retention of supF. λ infection of these faster growing strains did not result in λ-Tn5supF transposition derivatives, and further tests showed that the multicopy plasmids in these strains lacked the BamHI sites that flank supF in the parental plasmid. The large colony phenotype may thus be due to selection for cells with lower levels of suppressor tRNA; this may be achieved by Tn5supF transposition to the chromosome, deletion of supF from the multicopy plasmid, and segregation of cells with the supF-deleted plasmid.

A low-copy number plasmid containing Tn5supF and its nearby transposase gene was made by ligating a 3.1-kb EcoRI-Tth111I segment from pBRG1308 containing Tn5supF and the tnp gene to a 9-kb EcoRI-HindIII fragment containing the F factor-derived replication origin of the low-copy-number plasmid pDF41 [Kahn et al., supra.] (the 5' extension left by Tth111I and HindIII digestion are not complementary and were filled-in with the Klenow fragment of DNA polymerase I before ligation. The resultant plasmid, pBRG1310 (FIG. 2) was stable and was used as the donor plasmid in subsequent transpositions of Tn5supF to λ (See Results, below).

Transposition of Tn5supF to Amber Mutant Phage λ. Insertions of Tn5supF into the amber mutant phage Charon 4A [Williams & Blattner, J. Virol. 29, 555-575 (1979)] were obtained by infecting exponentially growing cells containing pBRG1310 at multiplicities of about one phage per cell and growing the infected cells for 90 min at 37° C. Aliquots of the lysate were plated on a lawn of sup$^o$ strain MC1061 to select for sup-independent phage. Since Charon 4A contains amber mutations in phage genes A and B, only phage with inserts of Tn5supF or amber+ revertants form plaques on MC1061.

Transposition of Tn5supF to Nonamber Phage. Because many λ phage vectors carry no amber mutations, an alternative selection was developed using the nonamber phage λb221 cI857. This phage was grown on pBRG1310-containing cells, as above, and derivatives containing Tn5supF were selected by plating on the dnaB-amber P1 ban strain DK21, obtained from D. M. Kurnit (Howard Hughes Medical Institute, University of Michigan, Ann Arbor, Mich.). This selection exploits the dependence of λ phage replication on the host dnaB function, and hence the inability of wild-type λ to form plaques on a dnaB-amber strain [D'Ari et al., J. Mol. Biol. 94, 341-366 (1975). Infection with supF-containing λ phage results in enough suppression of the dnaB amber mutation to permit phage replication and plaque formation. DK21, like other strains carrying dnaB alleles suppressed by the P1 ban gene, is cold-sensitive and makes relatively small colonies at 37° C. Mutants that formed faster growing colonies were present at frequencies of $10^{-5}$ to $10^{-3}$ in young cultures, caused a severe reduction in λ::Tn5supF plaque size, and thus were not suitable for the selection of Tn5supF transposition derivatives.

DNA Sequencing. Phage into which Tn5supF had transposed were plaque-purified once on the selective host strain (MC1061 or DK21, as appropriate); liquid lysates of the purified phage (5 ml) were grown on MC1061, and DNA was extracted in a conventional rapid "miniprep" procedure [Lutz et al., Proc. Natl. Acad. Sci. USA 84, 4379-4383 (1987)]. Phage DNA was denatured by heating 1 μg in 10 μL of distilled water to 100° C. for 3 min with a 100-fold molar excess of primer (about 15 pmol; 0.1 μg), quick-chilled on ice, and used for chain-termination DNA sequencing, either with reverse transcriptase [Zagursky et al., supra.] or Sequenase ™ DNA Polymerase (U.S. Biochemical Corp.) [Manfioletti & Schneider, Nucleic Acids Res. 16, 2873-2884 (1988), with comparable results. The sequencing results obtained with heat denaturation were generally better than those obtained with alkali denaturation of the phage DNA.

Results

Rationale. To be used for insertion mutagenesis and the sequencing of DNAs in phage λ a transposon should have the following characteristics: (i) transpose efficiently and relatively randomly; (ii) specify a trait that is easily selected during lytic growth; (iii) contain unique sequences near each end to serve as primer binding sites; and (iv) be very small, so that it will not make the λ DNA larger than the capacity of the phage head. Once transposed to the target DNA, it should not retranspose elsewhere. Tn5supF (FIG. 1) was designed to meet these criteria. As a derivative of Tn5, it should insert into many sites within a gene and exhibit less target specificity than most other transposons [Berg, Berg & Groisman in Mobile DNA, eds. Berg & Howe (Am. Soc. Microbiol., Washington, D.C.), pp. 879-925 (1989); Berg, Ibid., pp. 185-210]. It contains a supF amber-suppressor tRNA gene for selection, the 19-bp segments from the O and I ends of IS50(Tn5) that are needed for transposition [Berg in Mobile DNA, eds. Berg & Howe (Am. Soc. Microbiol., Washington, D.C.), pp. 185-210 (1989); Sasakawa et al., Proc. Natl. Acad. Sci. USA 80, 7293-7297 (1983); Johnson & Reznikoff, Nature 304, 280-282 (1983)] and a pair of BamHI sites, for easy restriction mapping of inserts; it is only 264 bp long, in contrast to the nearly 6 kb of wild-type Tn5. The 1.5-kb cis-acting transposase (tnp) gene [Isberg & Syvanen, J. Mol. Biol. 150, 15-32 (1981); Krebs & Reznikoff, Ibid. 192, 781-792 (1986)] is in the donor plasmid outside Tn5supF. Transposition of Tn5supF to λ phage was selected by plaque formation on appropriate host strains, as detailed below.

Figure 2:
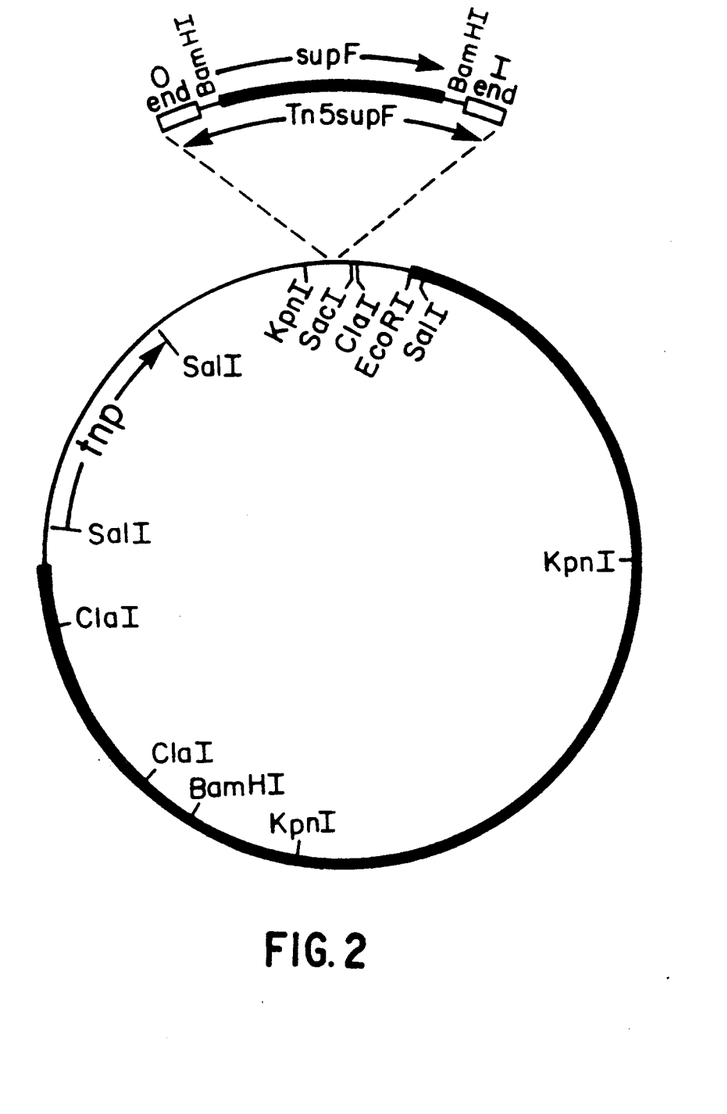

Characterization. Because the multicopy plasmid pBRG1308 that carried Tn5supF was unstable, a segment containing Tn5supF and the nearby tnp gene was cloned into pDF41, a derivative of the E. coli F factor (which is maintained at about one copy per chromosome), to generate pBRG1310 (FIG. 2). Cells carrying pBRG1310 formed large colonies, equivalent to those formed by plasmid-free cells (in antibiotic-free medium), and no loss of pBRG1310 was detected when overnight cultures were grown without selection for supF.

Transpositions of Tn5supF to the amber mutant phage Charon 4A were selected by infecting cells carrying pBRG1310 and plating the resulting lysate on the nonsuppressing (sup$^o$)strain MC1061. The frequency of Tn5supF transposition to Charon 4A was $2 \times 10^{-7}$ in strain DB4595 (Dam+) and $10^{-6}$ in strain DB4496 (Dam−). This is in accord with other studies showing that Tn5 transposition is decreased by Dam methylation [Dodson & Berg, Gene 67, 207-213 (1989); Yin et al., J. Mol. Biol. 199, 35-45 (1988). Burst-size measurements indicated that an average of three Tn5supF-containing phage were produced per cell from cells that produced any transposition products (total burst size, 60 phage per cell).

Many λ cloning vectors do not contain amber mutations in essential genes, and thus form plaques on sup⁰ MC1061. The do not form plaques on the dnaB-amber mutant strain DK21 because λ DNA replication depends on the host dnaB function [Furth et al., in Lambda II, eds. Hendrix et al., (Cold Spring Harbor Lab., Cold Spring Harbor, N.Y.), pp. 145-173 (1983)]. λ with inserts of supF, in contrast, does form plaques on DK21, due to suppression of the host dnaB-amber allele after phage infection. Inserts of Tn5supF into the nonamber phage λ b221 cI857 were selected on DK21. Phage able to form plaques on DK21 were obtained at a frequency of $3 \times 10^{-7}$ after a single cycle of phage growth in strain DB4495.

Figure 3:
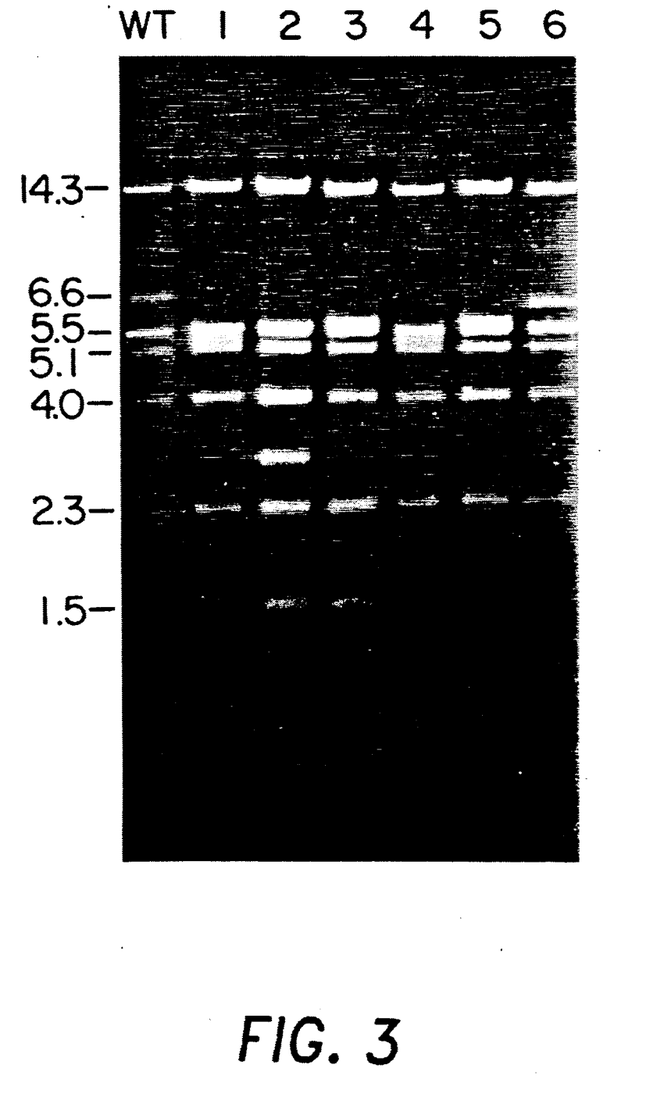

Analyses of Tn5supF-Containing Phage. The specificity of Tn5supF insertion was monitored genetically and physically. In plaque morphology tests using 5-bromo-4-chloro-3-indolyl β-D-galactoside (X-gal) medium [Williams & Blattner, *J. Virol.* 29, 555-575 (1979); Maniatis et al., supra.], 9 of 148 (6%) Tn5supF transposition derivatives of Charon 4A formed white (LacZ⁻) plaques, indicating insertion into lacZ; 30 LacZ⁻ plaques would have been expected if insertion had been completely random, since the 3-kb lacZ segment constitutes about one-fifth of the nonessential part of Charon 4A (Williams & Blattner, supra.). Digestions of the DNAs of Tn5supF-containing phage with BamHI (which cleaves Tn5supF and Charon 4A) plus EcoRI (which cleaves Charon 4A but not Tn5supF) confirmed that Tn5supF could insert into numerous target sites. Five separate sites of insertion are evident in the six phage shown in FIG. 3, with the isolates in lanes 3 and 5 possibly being siblings from a single insertion event.

Figure 4:
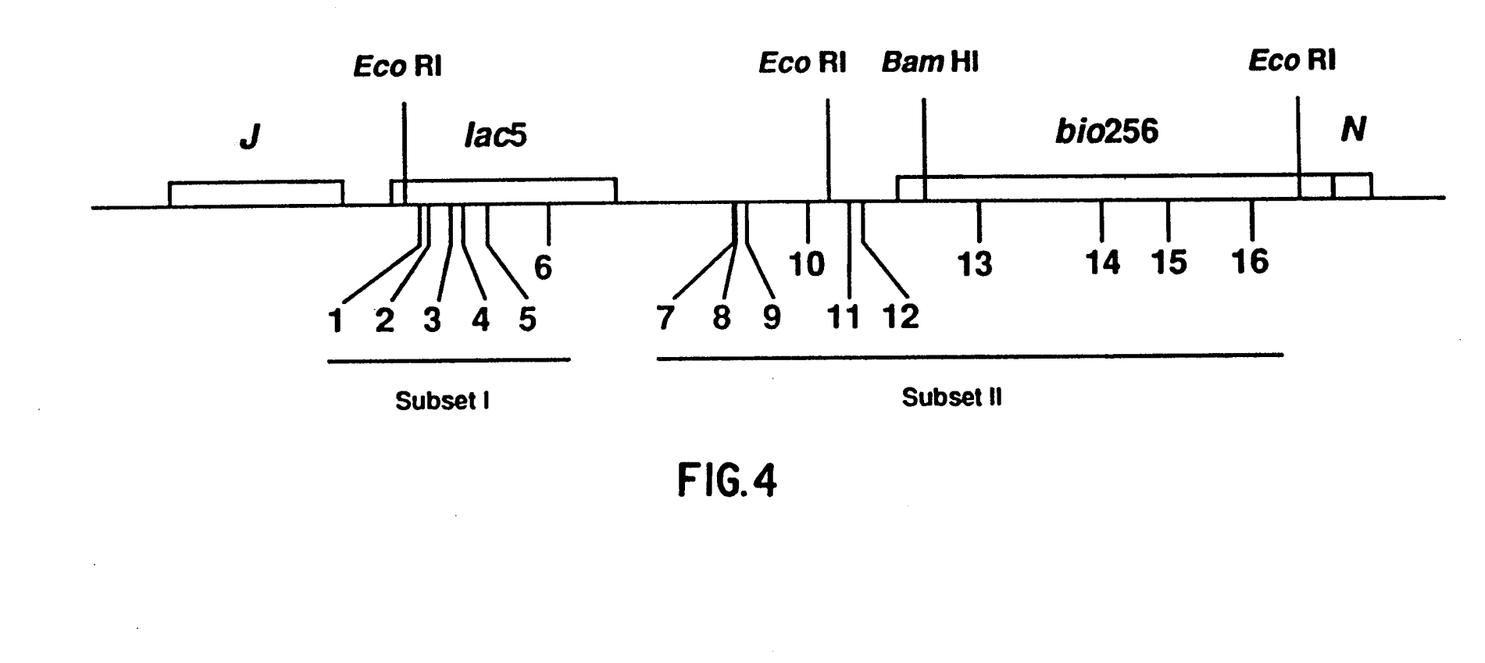

In another test the positions of 16 independent Tn5supF transpositions to Charon 4A were determined by restriction mapping and DNA sequencing (isolates 1-12) are shown in FIG. 4. The insertion events were widely distributed in the dispensable segments of Charon 4A, DNA sequencing from each end of Tn5supF in 12 Charon 4A::Tn5supF phage and also in seven Tn5supF transposition derivatives of λb221 c1857 (Table 2) showed that (i) no two insertions were at the same site (although inserts 7 and 8 in Charon 4A were separated by just a single base pair); (ii) 9 bp of the phage target sequence was duplicated by insertion at each site; and (iii) G+C pairs were present at each end of the duplicated segment in 9 cases, and at one end of the duplicated segment in the other 10 cases. None of the duplications contained A+T pairs at both ends, and no other features common to these insertion sites were found. An equivalent wide distribution of insertion sites and preference for G+C pairs at the ends of target duplications is also seen with other Tn5-based elements [Berg, in *Mobile DNA*, eds. Berg & Howe, (Am. Soc. Microbiol., Washington, D.C.), pp. 185-210, 1989); Berg et al., *Genetics* 105, 813-828 (1983); Lodge et al., *Ibid.* 120, 645-650 (1988)].

One of the seven λb221::Tn5supF phage (λb221 c1857 isolate 1, Table 2) is exceptional in containing Tn5supF in λ gene T, which is essential for phage tail formation. The insert created an in-frame TGA termination codon 11 codons before the end of gene T. Since this phage formed plaques the last 11 amino acids of T protein must not be essential for activity.

TABLE 2

| Tn5supF insertions in Charon 4A and λ b221 cI857 | | | |
|---|---|---|---|
| Insertion* | Position† | Duplicated sequence ‡ | Orientation§ |
| Charon 4A | | | |
| Subset I (lacZ portion) | | | |
| 1 | 1,663-1,671 | CATTTAATG | B |
| 2 | 1,803-1,811 | CTGAGCGCA | B |
| 3 | 2,026-2,034 | GCGGCGAGT | A |
| 4 | 2,328-2,336 | CCGTTGCTG | B |
| 5 | 2,588-2,596 | GGCGATGAG | B |
| 6 | 3,410-3,418 | GTCAGAAGC | A |
| Subset II (non-lacF portion) | | | |
| 7 | 25,199-25,217 | GGTTGTAGG | A |
| 8 | 25,226-25,234 | GTCGTAGGT | B |
| 9 | 25,445-25,453 | GGTTCGACC | A |
| 10 | 26,330-26,338 | GGGTTGGTG | A |
| 11 | 26,847-26,855 | CAAAGACAG | A |
| 12 | 26,928-26,936 | CTGCAGGAA | A |
| λ b221 cI857 | | | |
| 1 | 10,504-10,512 | GATGACAGT | A |
| 2 | 33,340-33,348 | CTCCTGGCT | B |
| 3 | 34,002-34,010 | GACATTGCT | B |
| 4 | 34,003-34,011 | ACATTGCTC | B |
| 5 | 34,636-34,644 | TTCCTCATG | A |
| 6 | 34,894-34,902 | AGCTTGGTG | B |
| 7 | 36,772-36,780 | GATCGGATC | B |

*Positions of insertions 1-12 (in Charon 4A) are diagrammed in FIG. 4.
† For insertions in lacZ (subset I), position refers to nucleotide sequence in the lac operon [Kalnins et al., EMBO J. 2, 593-597 (1983)]; for other insertions, position refers to nucleotide sequence in wild-type λ [Daniels et al., in Lambda II, eds. Hendrix et al., (Cold Spring Harbor Lab., Cold Spring, Harbor, N.Y.), pp. 519-676 (1983)].
‡ The 9 bp of target sequence duplicated by Tn5supF insertion. The sequences are presented 5' to 3' and correspond to the coding strand of lacZ (subset I), and the strand which is oriented left to right in λ.
§ Orientation A, λ-left 0-supF-I λ-right; orientation B, λ-left I-supF-0 λ-right.

The following are additional useful applications for Tn5supF and related elements: (i) Insertions of Tn5supF into plasmid or cosmid clones can be selected by suppression of a nonsense mutation in the tet and amp genes of the p3 plasmid used herein or in a chromosomal gene. (ii) Tn5supF derivatives containing diverse unique subterminal sequences can permit the "multiplex" sequencing of λ clones, equivalent to the highly efficient procedure developed for plasmid subclones [Church & Kieffer-Higgins, *Science* 240, 185-188 (1988)]. (iii) UGA stop codons are present in Tn5supF in each reading frame and in each orientation; inserts of Tn5supF should, therefore, interrupt translation and result in nested sets of amino-terminal peptides that can be useful in epitope mapping of complex proteins. (Iv) Systematic functional analyses of the *E. coli* genome should be feasible using derivatives of Tn5supF containing a reporter gene and a regulated promoter, a λ phage library of *E. coli* DNAs, and homologous recombination to put insertion mutant alleles into the bacterial chromosome.

Various other examples will be apparent to the person skilled in the art after reading the disclosure herein without departing from the spirit and scope of the invention. It is intended that all such other examples be included within the scope of the appended claims.

What is claimed is:
1. The plasmid pBRG1310.

* * * * *

UNITED STATES PATENT AND TRADEMARK OFFICE
CERTIFICATE OF CORRECTION

PATENT NO. : 5,316,946

DATED : MAY 31, 1994

INVENTOR(S) : SUHAS H. PHADNIS, et al.

It is certified that error appears in the above-identified patent and that said Letters Patent is hereby corrected as shown below:

On the title page, insert item: [75] Inventors, the name "Doulgas"

should read --Douglas--.

At col. 10, line 28 (last line of TABLE 2):

"GATCGGATC" should read --GATCGGATG--.

Signed and Sealed this

Thirty-first Day of October 1995

*Attest:*

BRUCE LEHMAN

*Attesting Officer*      *Commissioner of Patents and Trademarks*